US008841621B2

United States Patent
Nariyuki et al.

(10) Patent No.: US 8,841,621 B2
(45) Date of Patent: Sep. 23, 2014

(54) RADIOGRAPHIC IMAGING APPARATUS

(75) Inventors: Fumito Nariyuki, Kanagawa (JP); Haruyasu Nakatsugawa, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 134 days.

(21) Appl. No.: 13/326,992

(22) Filed: Dec. 15, 2011

(65) Prior Publication Data

US 2012/0153169 A1 Jun. 21, 2012

(30) Foreign Application Priority Data

Dec. 17, 2010 (JP) ................................. 2010-282271
Dec. 13, 2011 (JP) ................................. 2011-271952

(51) Int. Cl.
*G01T 1/202* (2006.01)
*H01L 27/146* (2006.01)
*G01T 1/20* (2006.01)
*A61B 6/00* (2006.01)

(52) U.S. Cl.
CPC ......... *H01L 27/14663* (2013.01); *A61B 6/4233* (2013.01); *G01T 1/2002* (2013.01)
USPC .................................................... 250/366

(58) Field of Classification Search
CPC ......... G01T 1/202; G01T 1/2002; G01T 1/20; G21K 4/00
USPC ......................................................... 250/366
See application file for complete search history.

(56) References Cited

U.S. PATENT DOCUMENTS

| 4,985,633 | A  | * | 1/1991  | Vieux et al. ................ 250/486.1 |
| 5,166,512 | A  | * | 11/1992 | Kubo ....................... 250/214 VT |
| 5,445,846 | A  | * | 8/1995  | Yoshida ........................... 427/65 |
| 5,449,449 | A  | * | 9/1995  | Vieux et al. ..................... 205/201 |
| 6,262,422 | B1 |   | 7/2001  | Homme et al. |
| 6,835,940 | B2 | * | 12/2004 | Morikawa et al. .......... 250/484.4 |
| 7,002,155 | B2 | * | 2/2006  | Miyata et al. ............ 250/370.11 |
| RE40,291  | E  |   | 5/2008  | Homme et al. |
| 7,514,698 | B2 | * | 4/2009  | Isoda .......................... 250/484.4 |
| 7,531,817 | B2 | * | 5/2009  | Nagata et al. ............... 250/483.1 |

(Continued)

FOREIGN PATENT DOCUMENTS

JP 09134689 A * 5/1997
JP 2000009846 A 1/2000

(Continued)

OTHER PUBLICATIONS

Notice of Reasons for Rejection, dated Feb. 26, 2013, issued in corresponding JP Application No. 2011-271952, 6 pages in English and Japanese.

(Continued)

*Primary Examiner* — Marcus Taningco
(74) *Attorney, Agent, or Firm* — Sughrue Mion, PLLC

(57) ABSTRACT

A radiographic imaging apparatus including: a scintillator that includes at least a columnar crystal and converts irradiated radiation into light; a light receiving element that receives light emitted from the scintillator; and a sensor substrate that comprises a light receiving element that receives light emitted from the scintillator and converts the received light into an electric signal, a cross-sectional diameter of the columnar crystal in a region located at a sensor substrate side being larger than that in a region located at a side opposite to the sensor substrate side.

12 Claims, 6 Drawing Sheets

(56) References Cited

U.S. PATENT DOCUMENTS

| | | |
|---|---|---|
| 2004/0126489 A1 | 7/2004 | Fuchs et al. |
| 2005/0067586 A1* | 3/2005 | Yanagita et al. ........... 250/484.4 |
| 2005/0077479 A1 | 4/2005 | Isoda et al. |
| 2007/0120061 A1* | 5/2007 | Kondo et al. ................. 250/367 |
| 2008/0054183 A1 | 3/2008 | Nagata et al. |
| 2011/0017913 A1 | 1/2011 | Kasai et al. |

FOREIGN PATENT DOCUMENTS

| | | |
|---|---|---|
| JP | 2001-330677 A | 11/2001 |
| JP | 3333278 B2 | 10/2002 |
| JP | 2004-125722 A | 4/2004 |
| JP | 2004117347 A | 4/2004 |
| JP | 2004-233343 A | 8/2004 |
| JP | 2005091222 A | 4/2005 |
| WO | 9836291 A1 | 8/1998 |
| WO | 2008029610 A1 | 3/2008 |
| WO | 2010023970 A1 | 3/2010 |

OTHER PUBLICATIONS

Notice of Reasons for Rejection, dated Oct. 8, 2013, issued in corresponding JP Application No. 2011-271952, 4 pages in English and Japanese.

* cited by examiner

RADIOGRAPHIC IMAGING APPARATUS

CROSS-REFERENCE TO RELATED APPLICATION

This application is based on and claims priority under 35 USC 119 from Japanese Patent Application No. 2010-282271, filed on Dec. 17, 2010, and Japanese Patent Application No. 2011-271952, filed on Dec. 13, 2011, the disclosures of which are incorporated by reference herein.

BACKGROUND

1. Technical Field

The present invention relates to a radiographic imaging apparatus, which is used in an X-ray imaging apparatus for medical use or the like.

2. Related Art

FPD's (Flat Panel Detectors) that have a radiation sensitive layer disposed on a thin film transistor (TFT) active matrix substrate, detect irradiated radiation, such as X-rays, and directly convert this radiation into radiographic image data expressing the distribution of irradiated radiation amounts are being put into practice. Portable radiographic imaging apparatuses (sometimes referred to below as "electronic cassettes") that house a panel type radiation detector, such as one of the FPDs, a control section including a memory section, and a power source section, also being put into practice for storing in the image memory radiographic image data output from the radiation detector. The radiographic imaging apparatus, which may be either portable or fixed, is being rapidly distributed due to its advantage of enabling immediately verifying an image compared to conventional image plates.

Various types of such radiographic imaging apparatuses have been proposed. For example, an indirect type converts radiation into light in a single operation using a scintillator of, for example, CsI:Tl, GOS ($Gd_2O_2S$:Tb), or the like, converts the converted light into electric charges through a semiconductor layer, and then stores the electric charges.

The amount of radiation emitted when the radiographic imaging apparatus is preferably decreased when it is used, for example, in living bodies. A scintillator which emits a great amount of light and has high sensitivity has been desired in the field of optical detector. From that point of view, several radiographic imaging apparatuses were proposed (e.g., Japanese Patent No. 3333278 and Japanese Patent Application Laid-Open (JP-A) No. 2001-330677). Such a radiographic imaging apparatus is constructed by attaching a scintillator, made of crystals of CsI or the like, to an insulating substrate, and emits radiation from an optical detector side.

A CT apparatus having a scintillator having crystals, in which the crystals have a quadrangular pyramidal frustum-shape in view of improving uniformity of light emission, was also proposed (for example, see JP-A No. 2004-125722).

A preparation of a radiation image conversion panel in which a column diameter of a columnar crystal is made larger by improving a degree of vacuum and increasing a temperature of a substrate during forming a scintillator layer was also proposed (for example, see JP-A No. 2004-233343).

SUMMARY

With respect to scintillators such as those described in Japanese Patent No. 3333278 and JP-A No. 2001-330677, which include crystals, it is known in theory that sensitivity becomes higher as the thickness of the crystals increases. In practice, however, when the thickness of the crystals is increased up to a certain value, light is attenuated or scattered when it passes through the scintillator. This may cause insufficient sensitivity or blurring of an image. Therefore, additional improvement in sensitivity is required.

The scintillator described in JP-A No. 2004-125722 may provide insufficient emission efficiency, and the sensitivity thereof and the resolution of images obtained thereby may be unsatisfactory. Therefore, improvement in sensitivity is required therefor.

The present invention has been made in view of the above circumstances and provides a radiographic imaging apparatus which may have an excellent detection sensitivity and may provide an image having a favorable sharpness without increasing the thickness of a scintillator.

One exemplary embodiment of one aspect of the invention is (1) a radiographic imaging apparatus comprising: a scintillator that comprises a columnar crystal and converts irradiated radiation into light; a light receiving element that receives light emitted from the scintillator; and a sensor substrate that comprises a light receiving element that receives light emitted from the scintillator and converts the received light into an electric signal, a cross-sectional diameter of the columnar crystal in a region located at a sensor substrate side being larger than that in a region located at a side opposite to the sensor substrate side.

In the exemplary embodiment, since a columnar crystal having high light emission efficiency and including a region with a large cross-sectional diameter is used in the scintillator, high efficiency light emission may be achieved, and a high resolution image may be obtained with high sensitivity.

If a large cross-sectional diameter of a columnar crystal is maintained from the initial portion to the terminal portion during film formation, adjacent columnar crystals are fused with each other along with the growth of the crystals, and the independency of each of the columnar crystals may not be ensured. In contrast, in an exemplary embodiment of this aspect, the cross-sectional diameter of the columnar crystal is increased from the initial portion to the terminal portion during film formation. As a result, a columnar crystal having a sufficiently large diameter at the terminal portion may be obtained while the optical independency of the respective columnar crystals is maintained. In another exemplary embodiment of this aspect, the cross-sectional diameter of the columnar crystal is decreased from the initial portion to the terminal portion to a certain degree during film formation. As a result, a columnar crystal having a sufficiently large diameter at the terminal portios may be obtained while the optical independency of the respective columnar crystals is maintained.

When the optical independency of the columnar crystals are ensured, that is, when the space between the adjacent columnar crystals are ensured, the space functions as a guide for the emitted light, and as a result, the emitted light may be efficiently transmitted without diffusing, and as a result, image blurring may be suppressed.

Another exemplary embodiment of the aspect is (2) the radiographic imaging apparatus of (1), wherein the radiographic imaging apparatus satisfies $(A-B)/B \geq 0.1$, wherein A represents a largest cross-sectional diameter of the columnar crystal, and B represents a smallest cross-sectional diameter of the columnar crystal. When this condition is satisfied, the independency of the adjacent columnar crystals may be ensured, and the occurrence of image blurring may be effectively suppressed.

Another exemplary embodiment of the aspect is (3) the radiographic imaging apparatus of (1) or (2), wherein the radiographic imaging apparatus receives radiation that is incident from the sensor substrate side. In the exemplary embodiment, the region having high light emission efficiency and having a large cross-sectional diameter in the columnar crystal is present at the sensor substrate side, so that the light emission region and the light detection region are present in the vicinity with each other, whereby higher sensitivity may be achieved.

Another exemplary embodiment of the aspect is (4) the radiographic imaging apparatus of any one of (1) to (3), wherein the columnar crystal is formed by direct vapor deposition, and a region that is in the scintillator and is in the vicinity of the sensor substrate comprises an aggregate of the columnar crystal that has a small cross-sectional diameter.

Another exemplary embodiment of the aspect is (5) the radiographic imaging apparatus any one of (1) to (4), wherein: the radiographic imaging apparatus further comprises a non-columnar crystal region at the sensor substrate side of the columnar crystal; the radiographic imaging apparatus satisfies $0.1\ \mu m \le T \le 2 \times D\ \mu m$, wherein T represents a thickness of the non-columnar crystal region, and D represents an average cross-sectional diameter of the columnar crystal; and the radiographic imaging apparatus receives radiation that is incident from the side opposite to the sensor substrate side.

When the non-columnar crystal region having a specific thickness is provided at the side opposite to the radiation incidence side of the columnar crystals included in the scintillator, the non-columnar crystal region functions as a reflective layer. As a result, radiation which has transmitted to a side opposite to a light detector side is efficiently reflected at a deep portion of the columnar crystal. Therefore, efficiency of detection of emitted light may be further improved, and consequently, a high sharpness image may be detected with high sensitivity.

When the cross-sectional diameter of the columnar crystal and the thickness of the non-columnar crystal region satisfy the above conditions, the effect of the invention may be further improved.

Another exemplary embodiment of the aspect is (6) the radiographic imaging apparatus of (5), wherein: the radiographic imaging apparatus further comprises a non-columnar crystal region at the sensor substrate side of the columnar crystal; the radiographic imaging apparatus satisfies $0.1\ \mu m \le T \le 2 \times D\ \mu m$, wherein T represents a thickness of the non-columnar crystal region, and D represents an average cross-sectional diameter of the columnar crystal; and the radiographic imaging apparatus receives radiation that is incident from the side opposite to the sensor substrate side.

Another exemplary embodiment of the aspect is (7) the radiographic imaging apparatus of (5), wherein:

the columnar crystal is formed on a surface of the non-columnar crystal region by vapor deposition;

a maximum cross-sectional diameter of the columnar crystal in a region from an interface between the columnar crystal and the non-columnar crystal region to a portion at a height of 50% of the thickness of the scintillator is larger than an average diameter of the columnar crystal at the interface; and an average diameter of the columnar crystal in a region from a tip end of the columnar crystal to a portion at the height of 50% of the thickness of the columnar crystal portion is smaller than the maximum cross-sectional diameter of the columnar crystal in a region from an interface between the columnar crystal and the non-columnar crystal region to a portion at ae height of 50% of the thickness of the scintillator.

Another exemplary embodiment of the aspect is (8) the radiographic imaging apparatus of (5), wherein: a thickness of the scintillator is 300 μm or less; the radiographic imaging apparatus satisfies $0.1\ \mu m \le T \le 0.5 \times D\ \mu m$, wherein T represents the thickness of the non-columnar crystal region and D represents the average cross-sectional diameter of the columnar crystal; and the radiographic imaging apparatus receives radiation that is incident from the side opposite to the sensor substrate side. Due to this configuration, higher sensitivity and resolution may be achieved. The radiographic imaging apparatus having this configuration may be suitable for mammography, which requires suppressing effects of radiation on the human body.

Another exemplary embodiment of the aspect is (9) the radiographic imaging apparatus of any one of (1) to (4), wherein: the radiographic imaging apparatus further comprises a non-columnar crystal region at the sensor substrate side of the columnar crystal; the radiographic imaging apparatus satisfies $0.1\ \mu m \le T \le 3 \times D\ \mu m$, wherein T represents a thickness of the non-columnar crystal region, and D represents an average cross-sectional diameter of the columnar crystal; and the radiographic imaging apparatus receives radiation that is incident from the sensor substrate side.

When the non-columnar crystal region having a specific thickness is provided at the radiation incidence side of the columnar crystals included in the scintillator, efficiency of detection of emitted light is further improved. Consequently, a high sharpness image may be detected with high sensitivity.

When the average cross-sectional diameter of the columnar crystal and the thickness of the non-columnar crystal region satisfy the above conditions, the effect of the invention may be further improved.

Another exemplary embodiment of the aspect is (10) the radiographic imaging apparatus of (9), wherein the columnar crystal is formed on a surface of the non-columnar crystal region by vapor deposition, and the columnar crystal is formed under at least one of the conditions of:

an atmospheric temperature for forming a part of the columnar crystal which is 20 μm-apart from the sensor substrate is higher than a temperature of the sensor substrate at the time of starting the formation of the non-columnar crystal region; or a degree of vacuum for forming a part of the columnar crystal which is apart from the sensor substrate by 20 μm or more is higher than a degree of vacuum of the sensor substrate at the time of starting the formation of the non-columnar crystal region.

Another exemplary embodiment of the aspect is (11) the radiographic imaging apparatus of (9), wherein the columnar crystal is formed on a surface of the non-columnar crystal region by vapor deposition;

a maximum cross-sectional diameter of the columnar crystal in a region from an interface between the columnar crystal and the non-columnar crystal region to a portion at a height of 50% of the thickness of the columnar crystal portion is larger than an average diameter of the columnar crystal at the interface; and an average diameter of the columnar crystal in a region from a tip end of the columnar crystal to a portion at the height of 50% of the thickness of the columnar crystal portion is smaller than the maximum cross-sectional diameter of the columnar crystal in a region from an interface between the columnar crystal and the non-columnar crystal region to a portion at ae height of 50% of the thickness of the columnar crystal portion.

Another exemplary embodiment of the aspect is (12) the radiographic imaging apparatus of (9), wherein: a thickness of the scintillator is 300 μm or less; the radiographic imaging apparatus satisfies $0.1\ \mu m \le T \le 1 \times D\ \mu m$, wherein T represents the thickness of the non-columnar crystal region, and D represents the average cross-sectional diameter of the columnar crystal; and the radiographic imaging apparatus receives radiation that is incident from the sensor substrate side. Due to this configuration, higher sensitivity and resolution may be achieved. The radiographic imaging apparatus having this configuration may be suitable for mammography, which requires suppressing effects of radiation on the human body.

Another exemplary embodiment of the aspect is (13) the radiographic imaging apparatus of any one of (1) to (12), wherein the scintillator comprises a crystal comprising CsI: Tl. In view of controlling the thickness and the cross-sectional diameters of the columnar crystals, it is preferable that the scintillator including such crystals is formed on a support or a TFT substrate by vapor deposition.

The radiographic imaging apparatus according to exemplary embodiments of the present invention may provide an excellent detection sensitivity and may provide an image having a favorable sharpness without increasing the thickness of a scintillator by having the configuration described above.

The radiographic imaging apparatus according to exemplary embodiments of the present invention may be applicable as an imaging apparatus for mammography. Contribution of emitted light at the emission side of a scintillator is large in mammographic imaging because X-ray energy used therein is low. When the radiographic imaging apparatus according to exemplary embodiments of the present invention is used as an imaging apparatus which irradiates radiation to a light-detection substrate side, emitted light at the emission side of a scintillator may be increased, which may be preferable for mammographic imaging.

DETAILED DESCRIPTION

Detailed explanation follows regarding exemplary embodiments for implementing the invention with reference to the accompanying drawings.

A radiographic imaging apparatus according to an exemplary embodiment of the invention is used in an X-ray imaging apparatus or the like. The radiographic imaging apparatus includes an emission layer, which emits light when radiation is irradiated thereon, and a sensor substrate, which includes a light-receiving element which converts the light of the emission layer. When the radiation, which contains image information, is irradiated on the radiographic imaging apparatus, it records the image information and outputs an image signal, which represents the recorded image information.

The sensor substrate includes at least the light-receiving element, and in embodiments, it may or may not further include a thin film transistor element (TFT element) which outputs an electric signal converted by the light-receiving element, a complementary metal oxide semiconductor image sensor element (CMOS element) and/or the like.

Figure 1:
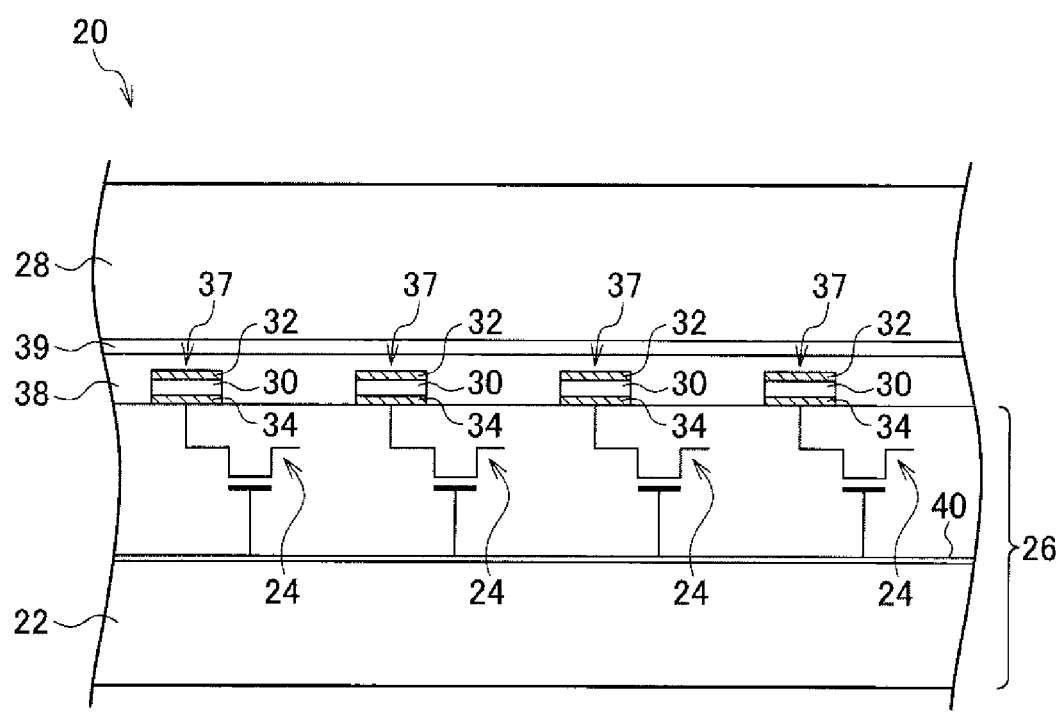
FIG. 1 is a cross-section showing a configuration of a radiation detector panel according to an exemplary embodiment.

As shown in FIG. 1, the radiation detection panel 10 according this exemplary embodiment includes a TFT substrate 26 with switch elements 24 formed on an insulating substrate 22. Each of the switch elements 24 is constructed with a thin-film transistor (TFT).

A scintillator layer 28 is formed over the TFT substrate 26, serving as an example of a radiation conversion layer and converting irradiated radiation into light.

Examples of a material that can be employed as the scintillator layer 28 include crystals of thallium-activated cesium iodide (CsI:Tl), terbium-activated gadolinium oxysulfide ($Gd_2O_2S$:Tb (GOS)), thallium-activated sodium iodide (NaI: TO, or sodium-activated cesium iodide (CsI:Na). Note that the scintillator layer 28 is not limited to those formed of these materials. Among these, a scintillator layer which is formed by using CsI:Tl may be preferable in consideration that emission spectrum matches the maximum value (in the vicinity of 550 nm) of the spectral sensitivity of an a-Si photodiode and that aging deterioration due to humidity rarely occurs.

Examples of a material that can be employed for forming the insulating substrate 22 include a glass substrate, various types of ceramic substrate, and a resin substrate. The insulating substrate 22 is also not limited to these materials.

In embodiments, the wavelength region of emission light from the scintillator layer 28 may be in the range of the visible light region (wavelengths from 360 nm to 830 nm), and in embodiments, such wavelength region of emission light may preferably include a green wavelength region to enable monochrome image capture with the radiation detection panel 20.

Specifically, fluorescent bodies employed in the scintillator layer 28 may preferably include cesium iodide (CsI) for cases in which X-rays are employed as radiation, and may further preferably use thallium doped cesium iodide (CsI(Tl)) having an emission spectrum during X-ray irradiation of wavelength 420 nm to 700 nm. The emission peak wavelength of CsI (Tl) in the visible light region is at 565 nm.

In certain embodiments in which the the scintillator layer is to be formed, for example, by columnar crystals of CsI (Tl) or the like, the scintillator layer 28 may be formed by vapor deposition onto a substrate. An Al plate may be often employed for the substrate for vapor deposition in cases in which the scintillator layer 28 is formed by vapor deposition, due to its X-ray transmissivity and cost perspective, however the material for the substrate is not limited thereto. In cases in which GOS is employed as the scintillator layer 28, the scintillator layer 28 may be formed by coating GOS on the front face of the TFT substrate 26 in place of using a substrate for vapor deposition.

Figure 4:
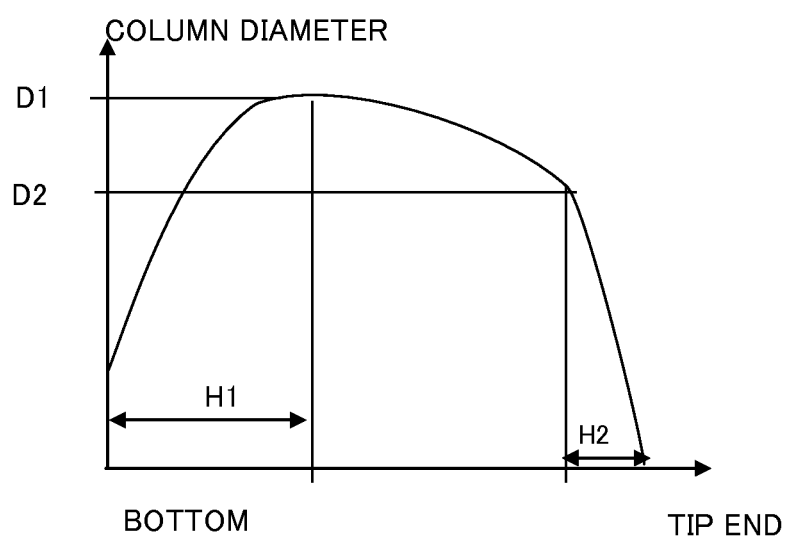
FIG. 4 is an exemplary diagram showing a relationship between a distance and a column diameter of a columnar crystal, in which the distance is that from a position of the columnar crystal, which is below a tip end of the columnar crystal, to a bottom of the columnar crystal which is in the vicinity of a surface of a substrate for vapor deposition, and the column diameter of the columnar crystal is that measured at the position, in a case in which the columnar crystal is formed by vapor deposition with a certain temperature and a certain degree of vacuum.

Details of an embodiment in which the columnar crystal of the scintillator layer 28 is formed by vapor deposition, which is a typical method of gas phase growth, is herein explained. FIG. 4 is an exemplary diagram showing a relationship between a distance (expressed by a horizontal axis) and a column diameter of a columnar crystal (expressed by a vertical axis), in which the distance is that between a position of the columnar crystal, which is below a tip end of the columnar crystal, and a surface of a substrate for vapor deposition, and the column diameter of the columnar crystal is that measured at the position, in a case in which the columnar crystal is formed by vapor deposition with a certain temperature and a certain degree of vacuum. In FIG. 4, H1, which is a portion at which a columnar diameter of the crystal column D1 becomes maximum (D1, which may be typically of, for example, about 7 μm) may be typically in a range of, for example, from 30% to 50% of a region from a bottom of the scintillator layer 28, which includes both the non-columnar portion and the columnar portion, to a tip end of the columnar crystal. H2, which is a portion of a pointed tip end of the column crystal formed by vapor deposition, may typically exist within a region of 30 μm or less apart from a vapor deposition completion surface of the scintillator layer 28. D2, which is a column diameter at a bottom of the portion of the pointed tip end of the column crystal formed by vapor deposition, may be typically of, for example, about 5 μm. Note that the concrete numerical values do not limit the scope of the invention.

The technique of directly providing a crystal on a surface of a TFT substrate or a surface of a primary layer over a substrate by subjecting such surface to vapor deposition may be sometimes referred to as "direct vapor deposition" hereinafter.

Figure 3:
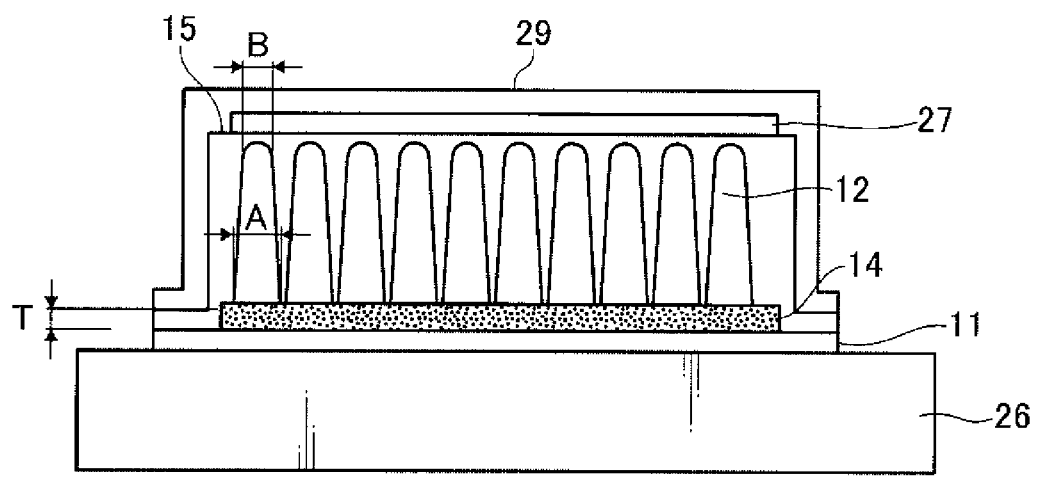
FIG. 3 is a perspective view showing a configuration of a second exemplary embodiment of a scintillator layer of the radiation detector panel shown in FIG. 1.

As is shown in FIG. 4, the column diameter may tend to become larger as a degree of vacuum improves or a temperature of the substrate increases. When these conditions for vapor deposition are not regulated, since the degree of vacuum tends to be better as the vapor deposition progresses, the column diameter may become excessively large to result in contacts and fusions of adjacent columnar crystals, which may cause image blurring due to light diffusion. In consideration of this, at least one or both of the degree of vacuum and the temperature of the substrate may be regulated in vapor deposition so that adjacent columnar crystals do not contact with each other even in embodiments in which the column diameter of the columnar crystal is larger at a position nearer its tip end side than that at a position nearer its substrate end. In this regard, FIG. 3 shows a configuration of the scintillator layer 28 of such embodiments, in which the scintillator layer 28 is formed by direct vapor deposition.

As is understood from FIG. 4, at the beginning of formation of the columnar crystals, the columnar crystals may be formed at high density in the vicinity of the surface of the substrate with respectively having a small column diameter, such as that in a range of 1 μm to 3 μm, and these columnar crystals may fuse with each other to provide an effect which is similar to that obtained when a non-columnar crystal region, which is explained below, is formed.

In a preferable exemplary embodiment in which a non-columnar crystal region is formed on the substrate and the columnar crystals are formed on the non-columnar crystal region, it may be generally preferable that at least one or both of the conditions that: an atmospheric temperature for forming parts of the columnar crystals which are apart from the substrate (for example, 20 μm-apart from the substrate) is higher than a temperature of the substrate at the time of starting the formation of the non-columnar crystal region; and a degree of vacuum for forming parts of the columnar crystals which are apart from the substrate (for example, 20 μm-apart from the substrate) is higher than a degree of vacuum of the substrate at the time of starting the formation of the non-columnar crystal region. When the scintillator layer 28 is formed by direct vapor deposition, a portion of the columnar crystal with the maximum column diameter, which is in the vicinity of the non-columnar crystal region, exists in a position which is nearer to the TFT substrate 26 than a middle portion of the scintillator layer 28 in the thickness direction.

Figure 2:
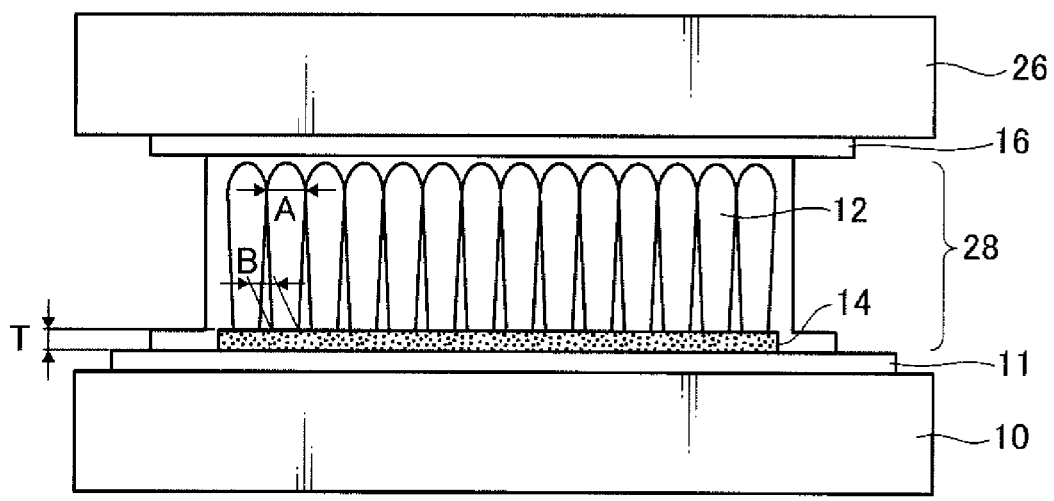
FIG. 2 is a perspective view showing a configuration of a first exemplary embodiment of a scintillator layer of the radiation detector panel shown in FIG. 1.

In another embodiment, as is shown FIG. 2, an additional substrate 16 may be provided and the scintillator layer 28 may be formed on a surface of the additional substrate 16 by vapor deposition. When the columnar crystal 12 is formed on the additional substrate 16, the columnar crystal 12 is made to have a column diameter which is larger at its tip end than at its portion in the vicinity of the non-columnar crystal region, and the additional substrate 16 having thus-made columnar crystal 12 adhere to the TFT substrate 26. Thereby, a portion of the columnar crystal with the maximum column diameter, which is apart from the non-columnar crystal region, exists in a position which is nearer to the TFT substrate 26 than a middle portion of the scintillator layer 28 in the thickness direction. In this regard, the technique of providing a crystal on a surface of an additional substrate 16 or a primary layer 11 which is formed on the additional substrate 16 by subjecting such surface to vapor deposition and adhering the thus-made scintillator layer 28 to a TFT substrate may be sometimes referred to as "indirect vapor deposition" hereinafter.

Photoconducting layers 30 are disposed between the scintillator layer 28 and the TFT substrate 26. The photoconducting layers 30 generate charge on being irradiated with light that has been converted by the scintillator layer 28. Bias electrodes 32 are formed on the surface of the photoconducting layers 30, on the scintillator layer 28 side thereof. The bias electrodes 32 apply a bias voltage to the photoconducting layers 30.

The photoconducting layers 30 absorb light that has been generated from the scintillator layer 28, and generates charge according to the light that has been absorbed. The photoconducting layers 30 may be formed from a material that generates charge on irradiation with light, and can, for example, be formed from amorphous silicon, an organic photoelectric conversion material, or the like. Photoconducting layers 30 containing amorphous silicon have a wide absorption spectrum and can absorb light that has been generated in the scintillator layer 28. Photoconducting layers 30 containing an organic photoelectric conversion material have an absorption spectrum with a sharp peak in the visible light region, and there is substantially no absorption by the photoconducting layers 30 of electromagnetic waves other than the light generated by the scintillator layer 28, thereby enabling effective suppression of noise generation by absorption of radiation, such as X-rays, in the photoconducting layers 30.

In order for an organic photoelectric conversion material configuring the photoconducting layers 30 to exhibit the most effective absorption of light generated in the scintillator layer 28, the absorption peak wavelength of the organic photoelectric conversion material is preferably as close as possible to the light generation peak wavelength of the scintillator layer 28. While ideally the absorption peak wavelength of the organic photoelectric conversion material matches the light generation peak of the scintillator layer 28, it is possible to achieve sufficient absorption of light emitted from the scintillator layer 28 as long as the difference between the two wavelengths is small. Specifically, the difference between the organic photoelectric conversion material absorption peak wavelength and the light generation peak wavelength of the scintillator layer 28 in response to radiation is preferably 10 nm or less, and more preferably 5 nm or less.

Examples of organic photoelectric conversion materials capable of meeting such criteria include quinacridone organic compounds and phthalocyanine organic compounds. For example, due to the peak absorption wavelength of quinacridone in the visible light region being 560 nm, it is possible to make the difference between the above two peack wavelengths 5 nm or less by employing quinacridone as the organic photoelectric conversion material and employing CsI (Tl) at the material for the scintillator layer 28. This enables substantially the maximum amount of charge to be generated in the photoconducting layers 30.

Charge collection electrodes 34 are formed on the TFT substrate 26 to collect charge that has been generated in the photoconducting layers 30. In the TFT substrate 26, the charge collected in each of the charge collection electrodes 34 is read by the switch elements 24.

Details of the photoconducting layers 30 applicable to the radiation detection panel 20 according to the present exemplary embodiment are as follows.

The electromagnetic wave absorption/photoelectric conversion parts in the radiation detection panel 20 may each have a configuration including a pair of electrodes, namely a collection electrode 34 and a bias electrode 32, and organic layers including one of the photoconducting layers 30 disposed between the collection electrode 34 and the bias electrode 32. More specifically, the organic layers have a configuration including, for example, a part for electromagnetic wave absorption, a part for photoelectric conversion, an electron transport part, a hole transport part, an electron blocking part, a hole blocking part, a crystallization prevention part, an electrode, an interlayer adhesion improvement part and the like, either superimposed on each other in layers or mixed.

The organic layers may preferably include a p-type organic compound or an n-type organic compound.

Organic p-type semiconductors (compounds) are mainly organic compounds that are donor organic semiconductors (compounds), typified by organic compounds with hole transport properties, and have the property that they readily donate electrons. More specifically they are organic compounds that have the smaller ionization potential when two organic materials are placed in contact with each other. Accordingly, any organic compound may be employed as a donor organic compound as long as it is an organic compound with electron donating properties.

Organic n-type semiconductors (compounds) are mainly organic compounds that are acceptor organic semiconductors (compounds), typified by organic compounds with electron transport properties, and have the property of readily accepting electrons. More specifically, they are organic compounds that have the larger ionization potential when two organic materials are placed in contact with each other. Accordingly, any organic compound may be employed as an acceptor organic compound as long as it is an organic compound with electron accepting properties.

Details regarding applicable materials for organic p-type semiconductors and organic n-type semiconductors to configure the photoconducting layers 30 are given in JP-A No. 2009-32854. In embodiments, the photoconducting layers 30 may further include a fullerene and/or a carbon nanotube.

Sensor portions 37 configuring each of the pixel portions at least include the collection electrode 34, the photoconducting layer 30, and the bias electrode 32. In embodiments, they may be preferably also provided with one or other of an electron blocking layer or a hole blocking layer in order to suppress dark current from increasing, and may be more preferably provided with both.

The electron blocking layer can be provided between the collection electrode 34 and the photoconducting layer 30 and may suppress an increase of dark current due to electrons being injected into the photoconducting layer 30 from the collection electrode 34 when a bias voltage is applied between the collection electrode 34 and the bias electrode 32.

An electron donor organic compound can be included in the electron blocking layer.

The material actually employed as the electron blocking layer may be selected according to the material of the adjacent electrode and material of the adjacent photoconducting layer 30. In embodiments, a material may be preferably employed having an electron affinity (Ea) that is at least 1.3 eV more than the work function (Wf) of the material of the adjacent electrode, and an ionization potential (Ip) that is about the same as, or smaller than, the Ip of the material of the photoconducting layer 30. Details regarding applicable materials as such an electron donor organic material are given in JP-A No. 2009-32854.

The thickness of the electron blocking layer may be preferably in a range of from 10 nm to 200 nm in view of reliably exhibiting a dark current suppressing effect and also to suppress a drop in photoelectric conversion efficiency of the sensor portions 37. The thickness may be more preferably in a range of from 30 nm to 150 nm, and even more more preferably in a range of from 50 nm to 100 nm.

The hole blocking layer can be provided between the photoconducting layer 30 and the bias electrode 32 and may suppress an increase of dark current due to holes being injected into photoconducting layer 30 from the bias electrode 32 when a bias voltage is applied between the collection electrode 34 and the bias electrode 32.

An electron acceptor organic compound can be included in the hole blocking layer.

The thickness of the hole blocking layer may be preferably in a range of from 10 nm to 200 nm in view of reliably exhibiting a dark current suppressing effect and also to suppress a drop in photoelectric conversion efficiency of the sensor portions 37. A thickness thereof of 30 nm to 150 nm may be more preferable, and a thickness of 50 nm to 100 nm may be even more preferable.

The material actually employed as the hole blocking layer may be selected according to the material of the adjacent electrode and material of the adjacent photoconducting layer 30. A material may be preferably employed having an ionization potential (Ip) that is at least 1.3 eV more than the work function (Wf) of the material of the adjacent electrode, and an electron affinity (Ea) that is about the same as, or greater than, the Ea of the material of the photoconducting layer 30. Details regarding applicable materials as such an electron acceptor organic material are given in JP-A No. 2009-32854.

Note that the position of the electron blocking layer and the hole blocking layer may be reversed in cases in which there is a bias voltage set such that holes from charges generated in the photoconducting layer 30 move into the bias electrode 32, and electrons from the charges move into the collection electrode 34. The electron blocking layer and the hole blocking layer may both be provided, or alternatively, one of the electron blocking layer and the hole blocking layer may be provided. A certain degree of dark current suppressing effect can be obtained as long as one of these layers is provided.

The TFT substrate 26 is adhered to a scintillator layer 28, which converts incident radioactive rays into light, via a primary layer 11 interposed therebetween. The scintillator layer 28 is formed on a support 10 as a radiation-converting layer that converts incident radioactive rays into light. The primary layer 11 may function as a protective layer for avoiding corrosion of the TFT substrate 26 due to the scintillator layer 28.

Details of the scintillator layer 28 of the exemplary embodiment are herein described with reference to FIG. 2.

In the exemplary embodiment, a columnar crystal 12 is present at the radiation incidence side of the scintillator layer 28. The columnar crystal 12 is formed such that a cross-sectional diameter thereof at a TFT element 26 side is larger than that at a substrate 10 side. In the exemplary embodiment, a non-columnar crystal region 14 of non-columnar crystals is present in the vicinity of the terminal portion of the columnar crystal 12 at a side opposite to the TFT element 26 side thereof. Note that, however, the non-columnar crystal region 14 may be either present or absent according to embodiments.

A high resolution image may be formed since a portion which has a larger cross-sectional diameter and thus provides efficient light emission in the columnar crystal 12 locates near the TFT element 26 which detects the light. Further, light diffusion may be suppressed and thereby image blurring may be suppressed since a space between adjacent columnar crystals 12 functions as a guide for the light. Further, the light which reaches a deep portion is reflected at the interface between the non-columnar crystal region 14 and the columnar crystal 12, and as a result, the detection efficiency of the emitted light may be further improved.

The scintillator layer 28 and the TFT element 26 are adhered via an adhesive layer 16.

When the columnar crystal 12 and the non-columnar crystal region 14 are provided as in the exemplary embodiment, T, which is the thickness of a non-columnar crystal region 14, may be preferably in a range of from 0.1 μm to 2×D μm, in which D represents an average cross-sectional diameter of the columnar crystal 12. In this configuration, radiation may be preferably incident from the side opposite to the TFT element 26 side, that is, from the substrate 10 side shown in FIG. 1.

When the non-columnar crystal region 14 is provided at the TFT substrate side as shown in FIG. 1, the adhesion between the non-columnar crystal region 14 and the substrate may be improved. In the exemplary embodiment, the non-columnar crystal region 14 may preferably have fewer voids therein as far as possible in view of suppressing undesirable reflection caused by the voids.

When these conditions are satisfied, the light emission efficiency in the scintillator thickness direction, suppression of light diffusion, and the region for reflecting light may be within preferable ranges, so that light emission efficiency, light detection efficiency and image resolution may be further improved.

Specifically, in embodiments in which: the thickness of the scintillator layer 28 is 300 μm or less, which may be typically in a range of from 100 μm to 300 μm and may be preferably in a range of from 150 μm to 250 μm; T is from 0.1 μm to 0.5×D μm; and radiation is incident from the side opposite to the TFT element 26 side, radiation detection sensitivity may be improved and a high resolution image may be formed with a weaker radiation irradiation, and thus such embodiments may be specifically suitable for mammography.

In other embodiments in which: the thickness of the scintillator layer 28 is 300 μm or less, which may be typically in a range of 100 μm to 300 μm and may be preferably in a range from 150 μm to 250 μm; T is from 0.1 μm to 1×D μm; and radiation is incident from the TFT element 26 side, may be also preferable in view of improving radiation detection sensitivity. Such embodiments may also provide a high resolution image with a weaker radiation irradiation and thus be suitable for mammography.

In the exemplary embodiment, the average cross-sectional diameter (D) of the columnar portion of the columnar crystal 12 may be preferably in a range of from 2 μm to 15 μm and more preferably in a range of from 4 μm to 10 μm in view of efficiently providing a light induction property.

The following inequality may be preferably satisfied.

$$(A-B)/B \geq 0.1$$

In the inequality, A represents a largest cross-sectional diameter of the columnar crystal 12, and B represents a smallest cross-sectional diameter of the columnar crystal 12.

When this inequality is satisfied, image sharpness may be further improved. (A−B)/B may be preferably 0.2 or more. This value is a relative value. In view of avoiding fusion of the columnar crystals, the difference between A and B may be preferably increased as the thickness of the columnar crystal 12 is increased.

The cross-sectional diameter of the columnar crystal herein means a value determined by measuring the diameter of the cross section prepared by cutting the columnar crystal in a direction perpendicular to the growth direction of the columnar crystal. Plural cross sections, which are prepared by cutting the columnar crystal with varying the cut positions along the growth direction of the columnar crystal are subjected to the measurement. The largest cross-sectional diameter obtained thereby is defined as A, the smallest cross-sectional diameter obtained thereby is defined as B, and the average of the thus-obtained plural cross-sectional diameters is defined as D. The plural cross-sections are at least 10 cross-sections. The largest cross-sectional diameter A may also be measured by observing the columnar crystal from the upper side to measure the largest diameter thereof Typically, ten cross sections, each of which having a surface perpendicular to the film thickness direction (crystal growth direction) of the columnar crystal, are prepared, and are observed by a scanning electron microscope (SEM) to measure the column diameters (cross-sectional diameters). Observation is performed at a magnification (about 2,000 times) that enables observing from 100 to 200 columnar crystals in one imaging, and the value of the maximum column diameter, the value of the minimum column diameter, and the value of the average column diameter are measured for each of the columnar crystals observed in one imaging. An average of the thus-measured maximum column diameters is defined as the maximum column diameter A, an average of the thus-measured minimum column diameters is defined as the minimum column diameter B, and an average of the thus-measured column diameters is defined as the average column diameter D. The column diameters (unit: micrometer) are read down to two decimal places, and the average is obtained by rounding off the numbers to one decimal place according to JIS Z 8401, that corresponds to ISO 31-0 1992.

A cross-section of a columnar crystal usually has an approximate round shape. When ten cross-sections of columnar crystals in a sample are found as being approximate round, the column diameter is defined as that obtained by measuring the cross-section in one direction. When a ross-section of a columnar crystal has a shape which can be hardly approximate to a round shape due to its crystal growth conditions or the like, the column diameter is defined as an average value of the maximum value and the minimum value obtained by measuring the cross-section.

The presence of the non-columnar crystal region 14 may be checked by obtaining a cross section in a direction parallel to the cross section of the columnar crystal obtained above, and observing it by an electron microscope. In the non-columnar crystal region, clear intervals between the crystals are rarely observed since the crystals irregularly combine with or overlap each other. A region in which crystals are adhered to each other in such a manner is regarded as the non-columnar crystal region. A line that binds vacancies (depressions) between adjacent crystals is a grain boundary, and column diameters and crystal cross-sectional diameters corresponding to the column diameters are measured by dividing the adhered crystals from each other so that they become minimum polygons. The crystal diameters are averaged in the same fashion as in the columnar crystal region, and the average is used.

The crystal cross-sectional diameters of the non-columnar crystals may be preferably in a range of from 0.2 μm to 7.0 μm in the viewpoint of effective reflection, and more preferably in a range of from 1.0 μm to 6.0 μm.

The crystal shape of the non-columnar crystals may be preferably substantially spherical and that the non-columnar crystal region may be preferably configured as a combination of crystals, which have a shape similar to a spherical shape (i.e., substantially spherical crystals) in view of reflection efficiency.

Also, in another preferable embodiments, at the beginning of formation of the columnar crystals, the columnar crystals may be formed at high density in the vicinity of the surface of the substrate with respectively having a small column diameter, such as that in a range of 1 μm to 3 μm, and these columnar crystals may fuse with each other to provide an effect which is similar to that of a non-columnar crystal region.

Details regarding a method for forming a columnar crystal having cross section diameters which are varied along a growth direction of crystal like that in the exemplary embodiment is explained below.

The scintillator layer 28, in which the area of the columnar crystals and the area of the non-columnar crystals are formed continuously, may be easily formed over the appropriate support 10 by a vapor deposition method, which will be described below.

The support 10 can be selected appropriately from the group consisting of a carbon plate, a carbon fiber reinforced plastic (CFRP), a glass plate, a quartz plate, a sapphire plate, a metal sheet, and the like. The metal sheet may be made of one selected from the group consisting of iron, tin, chromium, aluminum, and the like. The support 10 is not limited particularly to these examples as long as it can form the crystal regions, which form the scintillator layer 18, over the surfaces thereof. In embodiments, in consideration of cases in which radiation is applied to the radiographic imaging apparatus from the side of the support 10, the support 10 may be preferably transparent with respect to radiation applied thereto. For example, the support 10 may be preferably selected from those having a transparency of 80% or more with respect to radiation applied thereto.

The insulating substrate 12 may be selected from among, for example, a glass substrate, a variety of ceramic substrates, and a resin substrate. The insulating substrate 12 is not limited to these materials.

FIG. 3 is a schematic perspective view showing another exemplary embodiment of a scintillator layer 28. In this exemplary embodiment, a non-columnar crystal region 14 and a columnar crystal 12 are formed on a TFT substrate 26 via a primer layer 11. The columnar crystal 12 have a larger cross-sectional diameter at the TFT substrate 26 side, and the cross-sectional diameter is decreased as the distance from the TFT substrate 26 is increased. Also in the exemplary embodiment, the adjacent columnar crystals 12 are non-fused with each other. Each of the columnar crystals 12 is present independently.

In the exemplary embodiment, a scintillator protecting layer 15 is provided to cover the columnar crystal 12 and the non-columnar crystal region 14 in the scintillator layer 28.

The scintillator protecting layer 15 functions as a moisture barrier layer for supressing deliquescence of the columnar crystal 12 and the non-columnar crystal region 14, and also functions as a buffer layer for supressing corrosion of the reflective layer 27 provided adjacent to the scintillator layer 28.

A material having a barrier property against moisture in the air may be used as a component of the scintillator protecting layer 15. Examples thereof include an organic film obtained by a vapor phase polymerization such as a thermal chemical vapor deposition (CVD) or a plasma CVD. Examples of the organic film include a vapor phase polymerized-film formed from a polyparaxylylene resin by a thermal CVD, a plasma polymerized-film formed from a fluorine-containing compound and an unsaturated hydrocarbon monomer, and a plasma polymerized-film formed from an unsaturated hydrocarbon monomer. A layered structure of an organic film and an inorganic film may also be used, and preferable examples of a material of the inorganic film include a silicon nitride ($SiN_x$), a silicon oxide ($SiO_x$), a silicon oxynitride ($SiO_xN_y$), and $Al_2O_3$.

In the exemplary embodiment, a reflective layer protecting layer 29 is further provided to cover the scintillator protecting layer 15 and the reflective layer 27. The reflective layer protecting layer 29 functions as a layer for supressing decreasing of the reflectivity due to oxidation of the reflective layer 27 which is a metal thin film.

The reflective layer 27 functions to reflect the radiation incident from the TFT substrate 26 side. It usually has a rectangular plate shape, and is preferably formed of a material having high reflectivity, excellent dimensional stability and excellent heat resistance. Preferable examples of such a material include a metal selected from aluminum, a stainless steel, and the like, but are not limited thereto as far as the above conditions are satisfied.

A component of the reflective layer protecting layer 29 may be selected from oil and a coating agent such as a fluorine compound or a silicone compound, and the reflective layer protecting layer may be formed by appropriately coating it. In embodiments, in place of providing the reflective layer protecting layer 29, a surface of the reflective layer 27 may be polished and subjected to a smoothing treatment in view of protecting the reflective layer 27 by reducing the friction with the contact surface of the scintillator protecting layer 15.

In the exemplary embodiment, the absorption of radiation is relatively improved by increasing the cross-sectional diameter of the columnar crystal 12 at a region which is as nearer the TFT substrate 26 as possible during direct vapor deposition, whereby the sharpness of the formed image may be improved. Further, radiation incident from the TFT substrate 26 side is reflected by the reflective layer 27, so that radiation is also supplied from the back side (the side opposite to the radiation incidence side), whereby higher sensitivity may be achieved.

Also in the second exemplary embodiment, the following in equation may be preferably satisfied.

$$(A-B)/B \geq 0.1$$

In the inequation, A represents the largest cross-sectional diameter of the columnar crystal 12, and B represents the smallest cross-sectional diameter of the columnar crystal 12.

When this inequation is satisfied, the image sharpness may be further improved. In embodiments, $(A-B)/B$ may be more preferably 0.2 or more.

In the above two exemplary embodiments, when the columnar crystal 12 is formed from a material including CsI, a lower energy component of radiation such as X-ray is converted into visible light at a portion nearer to a radiation incidence side of the columnar crystal, and a higher energy component is converted into visible light at a deeper portion of the columnar crystal 12. Therefore, these exemplary embodiments may be suitable for mammography, in which imaging is carried out with a low energy component and a low irradiation dose.

Figure 5:
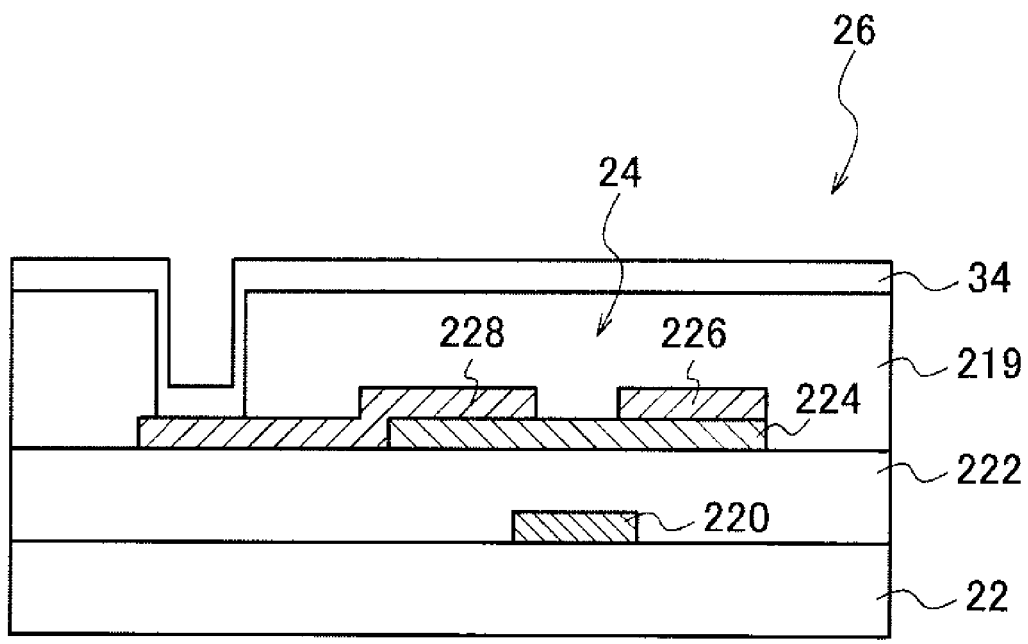
FIG. 5 is a perspective view showing a configuration of a switch element of a radiation detector according to an exemplary embodiment.

FIG. 5 shows a schematic configuration of the switch element 24.

The switch elements 24 are formed corresponding to the collection electrodes 34, and charge that has moved into the collection electrode 34 is converted into an electrical signal and output by the switch elements 24. The region in which each of the switch elements 24 is formed has a portion that overlaps with the collection electrode 34 in plan view. In this configuration, the switch elements 24 and the sensor portions 37 overlap along the thickness direction in each of the pixel portions. In view of minimizing the surface area of the radiation detection panel 20 (pixel portions), the regions formed with the switch elements 24 may be preferably completely covered by the collection electrodes 34.

Each of the switch elements 24 is formed with stacked layers of a gate electrode 220, a gate insulation film 222, and an active layer (channel layer) 224, further formed with a source electrode 226 and a drain electrode 228 spaced apart by a specific distance on the active layer 224.

The drain electrode 228 is electrically connected to the collection electrode 34 through a corresponding wiring line of an electrically conductive material formed so as to pass through an insulating layer 219 provided between the insulating substrate 22 and the collection electrode 34. Charge trapped by the collection electrode 34 can thereby be moved to the switch element 24.

The active layer 224 can be, for example, formed from amorphous silicon or a non-crystalline oxide, an organic semiconductor material, carbon nanotubes or the like. Note that the material for configuring the active layer 224 is not limited thereto.

Preferable examples of the non-crystalline oxide material capable of configuring the active layer 224 include oxides including at least one of In, Ga, and/or Zn (for example In—O oxides), more preferable examples thereof include oxides including two or more of In, Ga, and/or Zn (such as In—Zn—O oxides, In—Ga—O oxides, Ga—Zn—O oxides), and particularly preferable examples thereof include oxides including In, Ga and Zn. Preferable In—Ga—Zn—O oxides may be non-crystalline oxides which has a composition in a crystalline state of that represented by the formula $InGaO_3(ZnO)_m$ (where m is a positive integer less than 6), and that represented by $InGaZnO_4$ may be more preferable. Note that possible non-crystalline oxides for configuring the active layer 224 are not limited thereto.

Examples of the organic semiconductor material for configuring the active layer 224 include, but not limited to, phthalocyanine compounds, pentacene, vanadyl phthalocyanine and the like. Details regarding structures of such phthalocyanine compounds is given in JP-A No. 2009-212389.

By forming the active layer 224 of the switch elements 24 from a non-crystalline oxide or an organic semiconductor material formed with carbon nanotubes, noise generation in the switch elements 24 may be effectively suppressed, since there is no absorption of radiation such as X-rays, or any absorption is restricted to an extremely small amount.

When the active layer 224 is formed with carbon nanotubes, the switching speed of the switch elements 24 can be increased, and the switch elements 24 can be formed to have a low degree of absorption of light in the visible light region. In cases in which the active layer 224 is formed with carbon nanotubes, the purity of the carbon nanotubes is needed to be extremely high and thus the carbon nanotubes are needed to be prepared by separation or extraction by centrifugal separation or the like, since the performance of the switch elements 24 may deteriorate significantly with incorporation of only a minute amount of metal impurity in the active layer 224.

The non-crystalline compounds, organic semiconductor materials, carbon nanotubes and organic photoelectric conversion materials are all capable of being formed into a film at low temperature. Accordingly, the insulating substrate 22 is not limited to a substrate with high heat resistance, such as a semiconductor substrate, a quartz substrate, a glass substrate or the like. In embodiments, a flexible substrate, such as from a plastic, an aramid, or a bionanofiber substrate can be employed as the insulating substrate 22. Specific examples thereof include a flexible substrate from a polyester such as polyethylene terephthalate, polybutylene phthalate, polyethylene naphthalate or the like, polystyrene, polycarbonate, polyethersulphone, a polyarylate, a polyimide, a polycyclic olefin, a norbornene resin, and a poly (chloro trifluouro ethylene). By employing such a plastic flexible substrate, a reduction in weight can be achieved which may be beneficial to portability and the like.

In embodiments, an insulation layer to ensure insulation ability, a gas barrier layer for suppressing transmission of moisture and/or oxygen, an undercoat layer for flattening and/or raising adhesiveness to the electrodes, or other layers may be provided to the insulating substrate 22.

Since an aramid can be used in high temperature process applications of 200° C. or above, a transparent electrode material can be high-temperature hardened to give a low resistance, and compatibility can also be made to automatic packaging of driver ICs including solder re-flow processes. Since an aramid has a thermal expansion coefficient that is close to that of indium tin oxide (ITO) and glass substrate, post manufacture warping is small, and it is not readily broken. An aramid can also be formed in a relatively thin substrate in comparison to a glass substrate. In embodiments, the insulating substrate 22 may be formed with an aramid layered on an ultrathin glass substrate.

A bionanofiber composite is a composite of cellulose micro-fibril bundles (bacteria cellulose) produced by the bacterium Acetobacter Xylinum and a transparent resin. The cellulose micro-fibril bundles are, with a width of 50 nm, a size that is 1/10 that of visible wavelengths, and have high strength, high elasticity, and low thermal expansion. By impregnating and hardening the bacteria cellulose in a transparent resin, such as, for example, an acrylic resin, an epoxy resin, or the like, a bionanofiber composite is obtained with a light transmissivity of 90% to light at 500 nm wavelength, while including fibers at a proportion of 60% to 70%. The bionanofiber composite has a low thermal expansion coefficient (3 to 7 ppm/K), comparable to that of crystalline silicon, strength comparable to steel (460 MPa), high elasticity (30 GPa) and is also flexible. This enables the insulating substrate 22 to be formed thinner in comparison to configuration with a glass substrate or the like.

In this exemplary embodiment, the switch elements 24, the sensor portions 37 and the flattening layer 38 are formed in this sequence on the insulating substrate 22. The radiation detection panel 20 is formed by attaching the scintillator layer 28 above the insulating substrate 22 with the adhesive layer 39 employing a bonding resin of low light absorption. The insulating substrate 22 formed up to a transparent insulating layer 206 is referred to below as the TFT substrate 26.

Figure 6:
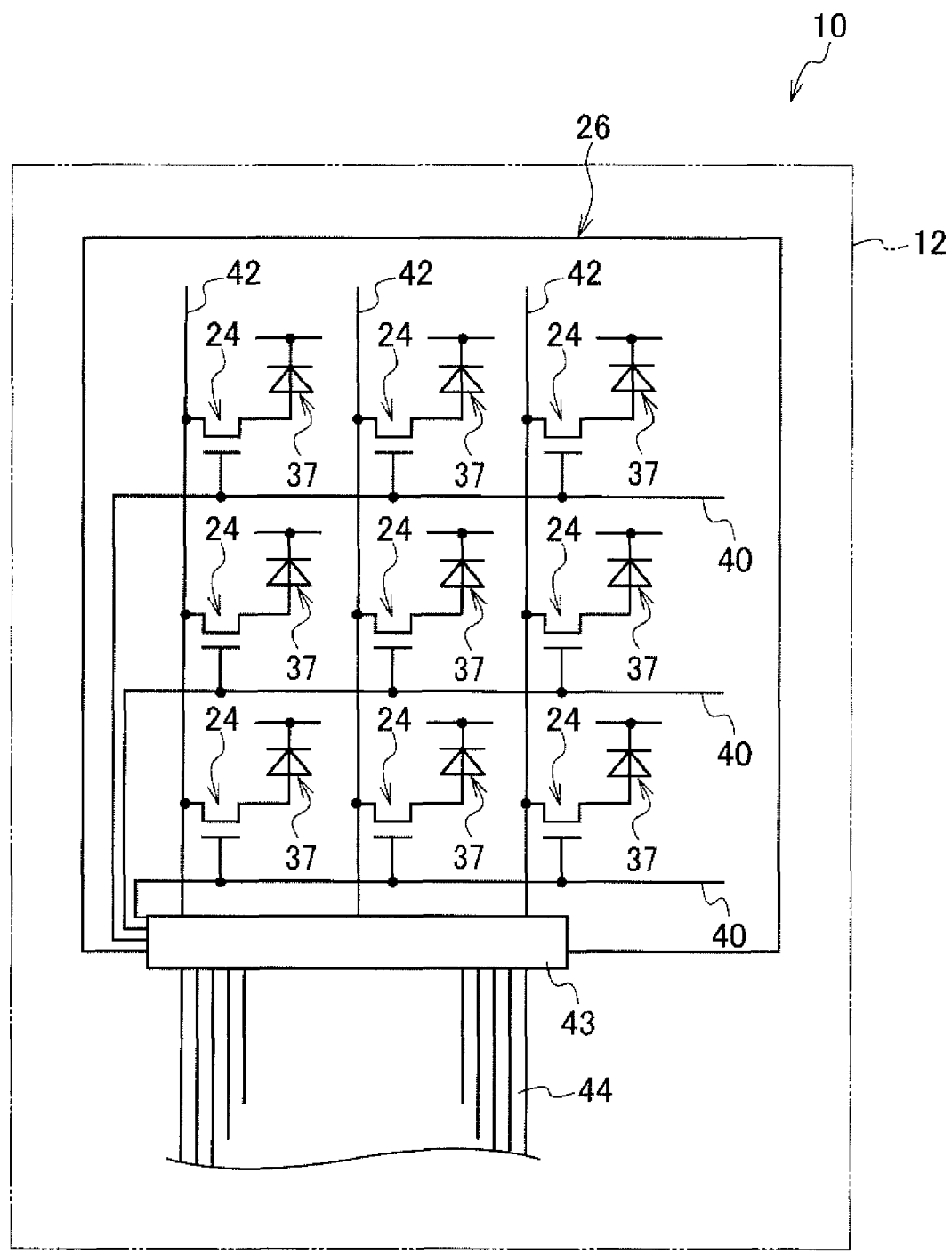
FIG. 6 is a view of circuit showing a configuration of a switch element of a radiation detector panel according to an exemplary embodiment.

The sensor portions 37, as shown in FIG. 6, has the charge collection electrodes 34 disposed in a two-dimensional shape on the TFT substrate 26, with the switch elements 24 disposed corresponding thereto in a two-dimensional shape on the insulating substrate 22.

In the TFT substrate 26 are provided: plural gate lines 40 extending in a given direction (row direction) for switching each of the switch elements 24 ON or OFF; and plural data lines 42 extending in a direction orthogonal to the gate lines 40 (column direction) for reading out charge through the switch elements 24 that are in the ON state.

A flattening layer 38 is formed in the TFT substrate 26 for flattening above the TFT substrate 26. An adhesive layer 39 is formed between the TFT substrate 26 and the scintillator layer 28 and above the flattening layer 38, for bonding the scintillator layer 28 to the TFT substrate 26.

The TFT substrate 26 is a quadrilateral shape in plan view, having 4 sides at the outside edges thereof. Specifically, the TFT substrate 26 is formed in a rectangular shape. A connection terminal 43 is disposed at one side of the peripheral edge of the TFT substrate 26 in plan view, connected to the individual gate lines 40 and the individual data lines 42. The connection terminal 43 is connected to the control section 50 through the connection wiring 44.

The radiographic imaging apparatus of this aspect may detect a radiation image with high sensitivity and high definition, and therefore be used for various apparatuses such as an X-ray imaging apparatus for medical diagnosis such as mammography, in which detection of a sharp image with a low irradiation dose is required. The radiographic imaging apparatus of this aspect may be used for a wide range of application, such as an X-ray imaging apparatus for industrial use for nondestructive inspection, or an apparatus for detecting particle rays ($\alpha$ ray, $\beta$ ray and $\gamma$ ray) other than electromagnetic wave.

A method of manufacturing a radiographic imaging apparatus, the method capable of efficiently manufacturing the radiographic imaging apparatus, is as follows.

In embodiments, it is preferable that the scintillator layer 28 may be formed directly over the surface of the support 10 or the TFT substrate 26 by a vapor deposition. The vapor deposition enables to continuously form the non-columnar crystal region and the columnar crystal region in sequence. Here, by way of example, a configuration made of CsI:Tl will be described.

The vapor deposition can be performed using a known method. In embodiments, it may be performed by evaporating CsI:Tl by heating using a means for flowing current through a resistive heating furnace or the like in the atmosphere at a degree of vacuum of from 0.01 Pa to 10 Pa, so that CsI:Tl is deposited over the support 10 that has a temperature of from room temperature (20° C.) to 300° C.

The columnar crystal having varied cross-sectional diameters in the above exemplary embodiments may be formed by, for example, starting from small diameters of the columnar crystal and then gradually increasing the diameter by increasing the application density of the heating means such as a heater. This method is described in JP-A No. 2003-66147, and the conditions described in this document may be used for carrying out the method.

When forming a crystal phase of CsI:Tl over the support 10 by vapor deposition, a cluster of relatively small crystals, which has a diameter corresponding to that of an indeterminate or substantially spherical crystal, is formed. When the vapor deposition is carried out, it is possible to grow the columnar crystal by the vapor deposition, continuously after the non-columnar crystal region is formed, by changing the condition of the degree of vacuum and/or the temperature of the support. That is, after the non-columnar crystal region is formed up to a certain thickness $t_2$, it is possible to efficiently grow and uniform columnar crystals using at least one of a means for raising the degree of vacuum and a means for raising the temperature of the support.

After the scintillator layer 28 is formed over the support 10, it is possible to produce the radiographic imaging apparatus by arranging the scintillator layer 28 to overlap the TFT substrate 26. The method of overlapping the scintillator layer 28 over the TFT substrate 26 is not specifically limited. Any method can be used as long as both are optically combined. As the method of arranging both to overlap, a method, which brings both into direct contact by arranging them opposite to each other, or a method, which brings both into contact via any of an adhesive layer or a planarizing layer, can be employed.

Examples of a method which brings both elements into direct contact includes a method of bringing the surface on the side of the scintillator layer 28 at which the columnar crystal region is present and the TFT substrate 26, which serves as the optical detector, into contact with each other by arranging them in opposition to each other after the scintillator layer 28 is formed over the support 10. The radiographic imaging apparatus may be manufactured by stacking and aligning both the scintillator layer 28 and the TFT substrate 26 in this manner. In the process of bringing the respective elements into contact with each other, it is not required to bring the surfaces of both elements into complete contact with each other. It may be allowable that depressions and protrusions formed by the crystals are present on the surface of the scintillator layer 28, as long as both can be optically combined with each other by being arranged one over the other. When light converted from radiation by the scintillator layer 28 is incident on the TFT substrate 26, the effects of the apparatus may be resulted therefrom.

In embodiments, the surface of the side of the formed scintillator layer 28, in which the area of columnar crystals 34 is present, and the optical detector 26 may be optically combined by being brought to be opposite to each other via a resin layer. Examples of the resin layer include a planarizing layer, which is for planarizing the surface of the scintillator layer 28, an adhesive layer, which fixedly brings both into contact, a matching oil layer, which is made of transparent liquid or gel, and the like. The resin, which forms the resin layer, is not specifically limited as long as it allows scintillation light, which is generated from the scintillator layer 28, to pass through to the optical detector 16 without reducing the light.

Examples of the resin, which forms the planarizing layer, include polyimide and parylene. Polyimide, which has good film-forming property, may be preferable.

The adhesive agent, which forms the adhesive layer, is not limited as long as those that are optically transparent to the scintillation light, which is generated from the scintillator layer 28. Examples of the adhesive agent include a thermoplastic resin, an ultraviolet (UV) curing adhesive agent, a thermosetting adhesive agent, a room-temperature curing adhesive agent, and a double-sided adhesive sheet. In view of not decreasing the sharpness of the image, it may be preferable to use an adhesive agent made of a low-viscosity epoxy resin since it can form an adhesive layer that is sufficiently thin in relation to the pixel size of the TFT substrate 26.

In embodiments, as described above, the thickness of the resin layer may be preferably 50 µm or less from the viewpoints of the sensitivity and image and more preferably in the range from 5 µm to 30 µm.

According to the manufacturing method as described above, it may be possible to efficiently and easily manufacture the radiographic imaging apparatus. In addition, the manufacturing method may also have an advantage capable of simply and easily manufacturing various specifications of scintillator layers according to designs by controlling the degree of vacuum and the temperature of the support in the forming of the film of the scintillator layer.

Exemplary embodiments of the invention are listed hereinbelow, although the invention is not limited thereby.

(1) A radiographic imaging apparatus comprising:
a scintillator that comprises a columnar crystal and converts irradiated radiation into light;
a light receiving element that receives light emitted from the scintillator; and
a TFT element that converts the received light into an electric signal, a cross-sectional diameter of the columnar crystal in a region located at a TFT element side being larger than that in a region located at a side opposite to the TFT element side.

(2) The radiographic imaging apparatus of (1), wherein the radiographic imaging apparatus satisfies $(A-B)/B \geq 0.1$, wherein A represents a largest cross-sectional diameter of the columnar crystal, and B represents a smallest cross-sectional diameter of the columnar crystal.

(3) The radiographic imaging apparatus of (1) or (2), wherein the radiographic imaging apparatus receives radiation that is incident from the TFT element side.

(4) The radiographic imaging apparatus of (1) or (2), wherein: the radiographic imaging apparatus further comprises a non-columnar crystal region at the TFT element side of the columnar crystal; the radiographic imaging apparatus satisfies $0.1 \, \mu m \leq T \leq 2 \times D \, \mu m$, wherein T represents a thickness of the non-columnar crystal region, and D represents an average cross-sectional diameter of the columnar crystal; and the radiographic imaging apparatus receives radiation that is incident from the side opposite to the TFT element side.

(5) The radiographic imaging apparatus of (4), wherein:
a thickness of the scintillator is in the range of from 100 μm to 300 μm;
the radiographic imaging apparatus satisfies $0.1 \, \mu m \leq T \leq 0.5 \times D \, \mu m$, wherein T represents the thickness of the non-columnar crystal region and D represents the average cross-sectional diameter of the columnar crystal;
the radiographic imaging apparatus receives radiation that is incident from the side opposite to the TFT element side; and
the radiographic imaging apparatus is used for mammography.

(6) The radiographic imaging apparatus of any one of (1) to (3), wherein: the radiographic imaging apparatus further comprises a non-columnar crystal region at the TFT element side of the columnar crystal;
the radiographic imaging apparatus satisfies $0.1 \, \mu m \leq T \leq 3 \times D \, \mu m$, wherein T represents a thickness of the non-columnar crystal region, and D represents an average cross-sectional diameter of the columnar crystal; and
the radiographic imaging apparatus receives radiation that is incident from the TFT element side.

(7) The radiographic imaging apparatus of (6), wherein:
a thickness of the scintillator is in the range of from 100 μm to 300 μm;
the radiographic imaging apparatus satisfies $0.1 \, \mu m \leq T \leq 1 \times D \, \mu m$, wherein T represents the thickness of the non-columnar crystal region, and D represents the average cross-sectional diameter of the columnar crystal;
the radiographic imaging apparatus receives radiation that is incident from the TFT element side; and
the radiographic imaging apparatus is used for mammography.

(8) The radiographic imaging apparatus of any one of (1) to (7), wherein the scintillator comprises a crystal comprising CsI and Tl.

EXAMPLES

The invention will be described in detail with respect to Examples, although the invention is not limited thereby.

Examples 1 and 2 and Comparative Example 1

1. Formation of Scintillator Layer
A non-alkali glass substrate (0.7 mm thick) was prepared as a support.
First, a support was surface-treated using Ar plasma for the purpose of improving adhesiveness with a CsI crystal layer. Afterwards, the surface-treated support was set in a vacuum chamber, which serves to form a scintillator film. The vacuum chamber included plural furnaces, which serve to heat raw materials, that is, CsI and TlI independently. After air was exhausted from the chamber, the degree of vacuum was set to be 0.75 Pa by introducing a certain amount of Ar. At a time point when the melting conditions of the raw materials were stabilized due to heating of the raw material furnaces, the support was rotated on a concentric circle by an apparatus tool of the vacuum apparatus, a shutter was opened, and deposition of an area of non-columnar crystals was started.

Film-forming was carried out under these conditions, and at a time point when the thickness of the non-columnar crystals became 10 μm, the degree of vacuum and the temperature were adjusted as shown in the following Table 1 so as to form columnar crystals having column diameters shown in Table 1.

In Examples 1 to 3, which are formed by direct vapor deposition, the non-columnar crystal 14 and the columnar crystal 12, which are directly formed on a surface of the primary layer 11 on the TFT substrate 26, configure the scintillator layer 28 as they are, and a portion of the columnar crystal 12 with the maximum column diameter exists in a position which is nearer to the TFT substrate 26 than a middle portion of the scintillator layer 28 in the thickness direction. In Example 4 and Comparative Example 1, which are formed by indirect vapor deposition, the non-columnar crystal 14 and the columnar crystal 12, which are formed on a surface of the additional substrate 16, configure the scintillator layer 28 by being adhered to the TFT substrate 26 so that a portion of the columnar crystal with the maximum column diameter exists in a position which is nearer to the TFT substrate 26 than a middle portion of the scintillator layer 28 in the thickness direction of the scintillator layer 28 as shown in FIG. 2.

In Table 1, the "x (μm)" means a distance from a "bottom" of the columnar crystal portion, which is an interface between the columnar crystal portion to the non-columnar crystal portion, to a portion which is the middle of the columnar crystal portion (that is, a portion at the height of 50% of the thickness of the columnar crystal portion). The "maximum columnar diameter of columnar crystal at region from x μm-upper to 20 μm-upper from bottom" shown in Table 1 means the maximum value of the columnar diameter of the columnar crystal of from x μm-upper to 20 μm-upper from the bottom of the columnar crystal. For example, when the thickness of the CsI columnar crystal portion is 500 μm, "x (μm)" becomes 250 μm.

In embodiments, a portion which provides a maximum value of the columnar diameter of the columnar crystal may be preferably within a region from a bottom of the scintillator layer 28, which includes both the non-columnar portion and the columnar portion, to the height of 50% or less of the thickness of the scintillator layer 28. Namely, the portion which provides the maximum value of the columnar diameter of the columnar crystal may preferably exist in a region nearer to the TFT substrate than the middle of the scintillator layer 28. In embodiments, the portion which provides the maximum value of the columnar diameter of the columnar crystal may be more preferably within a region from a bottom of the scintillator layer 28 to the height of 30% or less of the thickness of the scintillator layer 28.

Completion of formation of the columnar crystal portion by vapor deposition provides a pointed tip end to a column crystal. In consideration of this, Table 1 shows a column diameter of the columnar crystal at a portion of 30 μm-lower from a vapor deposition completion surface, which corresponds to the column diameter of the columnar crystal disregarding the pointed tip end of the column crystal. The information in Table 1 provide the shape of the columnar crystal portion which forms the scintillator layer 28 in each of Examples and Comparative Examples.

adjacent columnar crystals by regulating conditions for the direct vapor deposition so that the columnar crystal has a column diameter which is smaller in the vicinity of its tip end than its bottom. It is further remarked that Example 3 further improve the image blurring suppression effect by making a column diameter of a columnar crystal in the vicinity of its bottom being further smaller. Diffusion of light incident to the TFT substrate may be suppressed by making a column diameter of a columnar crystal in the vicinity of its bottom being further smaller. In contrast, light may incident to the TFT substrate in a diffusing state when a column diameter of a columnar crystal in the vicinity of its bottom is large.

The TFT substrate 26 and the scintillator layer 28 having the columnar crystal 12 and the non-columnar crystal region 14 formed under the above-described conditions are bound as shown in FIG. 1 by an engineering manner.

Afterwards, a TFT-driving circuit substrate and a charge-reading integrated circuit (IC) were attached to a terminal of the TFT substrate 26 via an anisotropic conductive film so as

TABLE 1

|  | Example 1 | Example 2 | Example 3 | Example 4 | Comparative Example 1 |
|---|---|---|---|---|---|
| Thickness of non-columnar crystal portion (μm) | 10 | 10 | 10 | 10 | 10 |
| Maximum column diameter of columnar crystal at portion of 20 μm-apart from bottom (μm) | 7 | 7 | 5 | 5 | 5 |
| Maximum column diameter of columnar crystal at region from x μm-upper to 20 μm-upper from bottom (μm) | 7 | 7 | 7 | 5 | 5 |
| Column diameter of columnar crystal at portion of 30 μm-lower from vapor deposition completion surface (μm) | 5 | 5 | 5 | 7 | 5 |
| Temperature of substrate for vapor deposition of non-columnar crystal (° C.) | 200 | 200 | 200 | 200 | 200 |
| Temperature of substrate for vapor deposition at portion of 20 μm-apart from bottom (° C.) | 240 | 280 | 200 | 200 | 200 |
| Temperature of substrate for vapor deposition at region from x μm-upper to 20 μm-upper from bottom (° C.) | 240 | 280 | 280 | 200 | 200 |
| Temperature of substrate for vapor deposition at vapor deposition completion (° C.) | 240 | 240 | 240 | 200 | 200 |
| Degree of vacuum at non-columnar crystal portion (Pa) | 0.1 | 0.1 | 0.1 | 0.1 | 0.1 |
| Degree of vacuum at portion of 20 μm-upper from bottom (Pa) | 1 | 1 | 1 | 1 | 1 |
| Degree of vacuum at region from x μm-upper to 20 μm-upper from bottom (Pa) | 1 | 1 | 1 | 1 | 1 |
| Degree of vacuum at vapor deposition completion (Pa) | 1.5 | 1 | 1 | 0.3 | 1 |
| Method of Vapor deposition | Direct | Direct | Direct | Indirect | Indirect |
| MTF | 98 | 98 | 98 | 98 | 100 |
| Sensitivity | 120 | 120 | 115 | 120 | 100 |
| Comprehensive evaluation | 118 | 118 | 115 | 118 | 100 |

It is remarked that as is understood from Table 1, Examples 1 to 3, which are formed by direct vapor deposition, respectively have a columnar crystal having a column diameter which is smaller in the vicinity of its tip end than its bottom which is nearer to the TFT substrate. This configuration is employed in view of suppressing occurrence of fusion of adjacent columnar crystals. The fusion of adjacent columnar crystals may highly possibly occur when direct vapor deposition is carried out since a column diameter may gradually grow larger as the direct vapor deposition progresses and a gap between adjacent columnar crystals may become smaller accordingly. The fusion of adjacent columnar crystals may bring about deterioration in light guiding effect, which may cause image blurring. Examples 1 to 3 suppress this fusion of to be connected to a circuit substrate, which serves to perform drive control and analog-digital (AD) conversion. Radiographic imaging apparatuses of Examples 1 and 2 and Comparative Example 1 were respectively manufactured by this procedure.

It was arranged so that radiation is incident from the optical detector 26 side, and reading of a radiation image was performed by controlling a scanning personal computer (PC), which was connected to the radiographic imaging apparatus via a cable.

2. Evaluation of Radiographic Imaging Apparatus
2-1. Sensitivity

X-rays were used for radiation. The optical detector 16 was driven using an electrical circuit when emitting the X-rays, and the amount of electric charges, generated from scintillated light through photoelectric transformation by a photodiode, were calculated by reading the electric charges, amplifying the electric charges using a charge amplifier, and then performing the AD conversion on the electric charges. An amount of electric charges (noises of the detection apparatus), which was read when X-rays were not being emitted, was measured in advance and was subtracted from an amount of electric charges, which was read when X-rays were being emitted, and the subtracted value was set as the sensitivity. The result is presented as a relative value when sensitivity in Comparative Example 1 was set as 100, which is described below. The sensitivity of Example 1 was 120.

2-2. Modulation Transfer Function (MTF)

An MTF curve was produced by calculating an edge shape, which was obtained by imaging the MTF edge made of tungsten (W), based on the IEC standard. The result was compared with the value 2 cycle/mm, and was presented as a relative value when the value of Comparative Example 1 was set as 100. The MTF of Example 1 was 100.

2-3. Adhesion

A sample formed by bonding the TFT substrate 26 and the scintillator layer 28 having the columnar crystal 12 and the non-columnar crystal region 14 formed under the above-described conditions by an engineering manner as described above was subjected to a thermal cycling test which repeats 100 cycles of heating, in which one heating cycle includes raising a temperature from −30° C. to 50° C. with a rate of +20° C./hour and then lowering the temperature from 50° C. to −30° C. with a rate of −20° C./hour. The resulted sample was observed for its interface between the scintillator layer 28 and the TFT substrate 26. A sample which exhibited no peeling, flooding or uneven adhesion was evaluated as being "good", and a sample which exhibited at least one of peeling, flooding and uneven adhesion was evaluated as being "unsatisfactory". Results are shown in Table 2.

2-4. Comprehensive Evaluation

The performance of the radiographic imaging apparatus was judged using a product of the evaluation results of the sensitivity and the MTF as an index. Comparative evaluation was performed with setting the result of Comparative Example 1 as 100. The results are shown in Table 1. It is preferable that the difference in the performance be clearly recognized when the image is subjectively evaluated as the product of the sensitivity and the MTF be 110 or more. The comprehensive evaluations of Examples 1 to 4 were 115 or 118 respectively, and it can be understood that the sensitivity and the sharpness of the image were better than those of Comparative Example 1.

Examples 5 and 6 and Comparative examples 2 to 4

Radiographic imaging apparatuses of Examples 5 and 6 and Comparative examples 2 to 4 were respectively prepared and evaluated in the similar manner as Example 1, except that the layer thickness of a non-colamunar portion and the average cross-sectional diameter of a colamunar portion are changed as shown in the following Table 2 by changing the vapor depostion condition. Results are shown in Table 2. In these Examples and Comparative examples, irradiation was provided so as to be incident from the substrate 11 side.

TABLE 2

| | Average column diameter (μm) | Thickness of scintillator (μm) | Thickness of non-columnar crystal portion (μm) | Incident direction | Adhesion | MTF | Sensitivity | Comprehensive evaluation |
|---|---|---|---|---|---|---|---|---|
| Example 5 | 7 μm | 600 μm | 7 μm | scintillator side-incidence | Good | 106 | 105 | 111 |
| Example 6 | 7 μm | 600 μm | 14 μm | scintillator side-incidence | Good | 103 | 103 | 106 |
| Comparative Example 2 | 7 μm | 600 μm | 21 μm | scintillator side-incidence | Good | 100 | 100 | 100 |
| Comparative Example 3 | 7 μm | 600 μm | 28 μm | scintillator side-incidence | Good | 96 | 98 | 94 |
| Comparative Example 4 | 7 μm | 600 μm | None | scintillator side-incidence | Unsatisfactory | 109 | 106 | 115 |

Examples 7 to 9 and Comparative Examples 5 and 6

Each of the radiographic imaging apparatuses of Examples 7 to 9 and Comparative Examples 5 and 6 was produced and evaluated in the similar manner as Example 1, except that the condition for vapor deposition was changed so as to provide the thickness of the non-columnar crystal portion and the average cross-sectional diameter of the columnar crystal as shown in the following Table 3 to form a scintillator layer, which was incorporated into a radiation irradiation apparatus as shown in FIG. 3. Results are shown in Table 3. In these Examples and Comparative examples, irradiation was provided so as to be incident from the TFT substrate 26 side.

TABLE 3

| | Average column diameter (μm) | Thickness of scintillator (μm) | Thickness of non-columnar crystal portion (μm) | Incident direction | Adhesion | MTF | Sensitivity | Comprehensive evaluation |
|---|---|---|---|---|---|---|---|---|
| Example 7 | 7 μm | 600 μm | 7 μm | Substrate side-incidence | Good | 109 | 107 | 116 |
| Example 8 | 7 μm | 600 μm | 14 μm | Substrate side-incidence | Good | 107 | 105 | 112 |

TABLE 3-continued

| | Average column diameter (μm) | Thickness of scintillator (μm) | Thickness of non-columnar crystal portion (μm) | Incident direction | Adhesion | MTF | Sensitivity | Comprehensive evaluation |
|---|---|---|---|---|---|---|---|---|
| Example 9 | 7 μm | 600 μm | 21 μm | Substrate side-incidence | Good | 105 | 102 | 107 |
| Comparative Example 5 | 7 μm | 600 μm | 28 μm | Substrate side-incidence | Good | 101 | 100 | 101 |
| Comparative Example 6 | 7 μm | 600 μm | None | Substrate side-incidence | Unsatisfactory | 111 | 108 | 120 |

As apparent from Tables 1 to 3, images produced from the radiographic imaging apparatuses of Examples 1 to 9 have high sensitivity and higher sharpness due to suppression of degradation in image quality, such as image blurring, comparing to those produced from Comparative Examples 1 to 6.

All publications, patent applications, and technical standards mentioned in this specification are herein incorporated by reference to the same extent as if such individual publication, patent application, or technical standard was specifically and individually indicated to be incorporated by reference. It will be obvious to those having skill in the art that many changes may be made in the above-described details of the preferred embodiments of the present invention. It is intended that the scope of the invention be defined by the following claims and their equivalents.

What is claimed is:

1. A radiographic imaging apparatus comprising:
a scintillator that comprises a columnar crystal and converts irradiated radiation into light; and
a sensor substrate that comprises a light receiving element that receives light emitted from the scintillator and converts the received light into an electric signal,
a cross-sectional diameter of a columnar portion of the columnar crystal in a region located at a sensor substrate side being larger than that in a region located at a side opposite to the sensor substrate side, the columnar portion excluding a pointed tip end of the columnar crystal,
wherein the radiographic imaging apparatus further comprises a non-columnar crystal region at the sensor substrate side of the columnar crystal;
the radiographic imaging apparatus satisfies 0.1 μm≤T≤3×D μm, wherein T represents a thickness of the non-columnar crystal region, and D represents an average cross-sectional diameter of the columnar crystal; and
the radiographic imaging apparatus receives radiation that is incident from the sensor substrate side, and
wherein a maximum cross-sectional diameter of the columnar crystal in a region from an interface between the columnar crystal and the non-columnar crystal region to a portion at a height of 50% of the thickness of the columnar crystal portion is larger than an average diameter of the columnar crystal at the interface; and
an average diameter of the columnar crystal in a region from a tip end of the columnar crystal to a portion at the height of 50% of the thickness of the columnar crystal portion is smaller than the maximum cross-sectional diameter of the columnar crystal in a region from an interface between the columnar crystal and the non-columnar crystal region to a portion at the height of 50% of the thickness of the columnar crystal portion.

2. The radiographic imaging apparatus of claim 1, wherein the radiographic imaging apparatus satisfies (A−B)/B≥0.1, wherein A represents a largest cross-sectional diameter of the columnar crystal, and B represents a smallest cross-sectional diameter of the columnar crystal.

3. The radiographic imaging apparatus of claim 1, wherein the radiographic imaging apparatus receives radiation that is incident from the sensor substrate side.

4. The radiographic imaging apparatus of claim 1, wherein a region that is in the scintillator and is in the vicinity of the sensor substrate comprises an aggregate of the columnar crystal that has a cross-sectional diameter of from 1 μm to 3 μm.

5. The radiographic imaging apparatus of claim 1, wherein:
the radiographic imaging apparatus further comprises a non-columnar crystal region at the sensor substrate side of the columnar crystal; the radiographic imaging apparatus satisfies 0.1 μm≤T≤2×D μm, wherein T represents a thickness of the non-columnar crystal region, and D represents an average cross-sectional diameter of the columnar crystal; and
the radiographic imaging apparatus receives radiation that is incident from the side opposite to the sensor substrate side.

6. The radiographic imaging apparatus of claim 5, wherein:
a maximum cross-sectional diameter of the columnar crystal in a region from an interface between the columnar crystal and the non-columnar crystal region to a portion at a height of 50% of the thickness of the columnar crystal portion is larger than an average diameter of the columnar crystal at the interface; and
an average diameter of the columnar crystal in a region from a tip end of the columnar crystal to a portion at the height of 50% of the thickness of the columnar crystal portion is smaller than the maximum cross-sectional diameter of the columnar crystal in a region from an interface between the columnar crystal and the non-columnar crystal region to a portion at the height of 50% of the thickness of the columnar crystal portion.

7. The radiographic imaging apparatus of claim 5, wherein:
a thickness of the scintillator is in the range of from 100 μm to 300 μm;
the radiographic imaging apparatus satisfies 0.1 μm≤T≤0.5×D μm, wherein T represents the thickness of the non-columnar crystal region and D represents the average cross-sectional diameter of the columnar crystal;
the radiographic imaging apparatus receives radiation that is incident from the side opposite to the sensor substrate side; and
the radiographic imaging apparatus is used for mammography.

8. The radiographic imaging apparatus of claim 1, wherein:
a thickness of the scintillator is in the range of from 100 μm to 300 μm;
the radiographic imaging apparatus satisfies 0.1 μm≤T≤1×D μm, wherein T represents the thickness of the non-columnar crystal region, and D represents the average cross-sectional diameter of the columnar crystal;

the radiographic imaging apparatus receives radiation that is incident from the sensor substrate side; and the radiographic imaging apparatus is used for mammography.

9. The radiographic imaging apparatus of claim 1, wherein the scintillator comprises a crystal comprising CsI and Tl.

10. The radiographic imaging apparatus of claim 1, wherein a portion of the columnar crystal at which a cross-sectional diameter of the columnar crystal is maximum exists in a position which is nearer to the sensor substrate than a middle portion of the scintillator in the thickness direction of the scintillator.

11. The radiographic imaging apparatus of claim 1, wherein a cross-sectional diameter of a columnar portion of the columnar crystal gradually varies along the thickness direction of the scintillator.

12. The radiographic imaging apparatus of claim 1, wherein a portion of the columnar crystal which is nearest to the sensor substrate provides a cross-sectional diameter which is smaller than the maximum cross-sectional diameter of the columnar crystal.

\* \* \* \* \*